United States Patent
Maddess et al.

(10) Patent No.: US 7,006,863 B2
(45) Date of Patent: *Feb. 28, 2006

(54) METHOD AND APPARATUS FOR ASSESSING NEURAL FUNCTION BY SPARSE STIMULI

(75) Inventors: Teddy Lee Maddess, Kaleen (AU); Andrew Charles James, Braddon (AU)

(73) Assignee: The Australian National University, Australian Capital Territory (AU)

( * ) Notice: Subject to any disclaimer, the term of this patent is extended or adjusted under 35 U.S.C. 154(b) by 0 days.

This patent is subject to a terminal disclaimer.

(21) Appl. No.: 10/239,971

(22) PCT Filed: Mar. 27, 2001

(86) PCT No.: PCT/AU01/00343

§ 371 (c)(1),
(2), (4) Date: Mar. 3, 2003

(87) PCT Pub. No.: WO01/72211

PCT Pub. Date: Oct. 4, 2001

(65) Prior Publication Data

US 2003/0163060 A1 Aug. 28, 2003

(51) Int. Cl.
*A61B 5/00* (2006.01)

(52) U.S. Cl. ............... 600/544; 600/546; 600/558; 600/559

(58) Field of Classification Search ........ 600/558–559, 600/544–546
See application file for complete search history.

(56) References Cited

U.S. PATENT DOCUMENTS 4,094,307 A 6/1978 Young, Jr.

(Continued)

FOREIGN PATENT DOCUMENTS

WO WO 92/19172 11/1992

(Continued)

OTHER PUBLICATIONS

Benardete, et al., "Contrast gain control on the primate retina: P cells are not X-like, some M cells are" *Visual Neuroscience* (1992) 8:483-486.

(Continued)

*Primary Examiner*—Robert L. Nasser
(74) *Attorney, Agent, or Firm*—Knobbe, Martens, Olson & Bear, LLP

(57) ABSTRACT

The present invention relates to a method and an apparatus for simultaneously assessing the functional status of component parts of the nervous system by presenting sparse stimuli to one or more parts of the sensory nervous system. Sparse stimuli consist of temporal sequences of stimulus conditions presented against a baseline null stimulus condition, where the non-null stimulus condition, or conditions, are presented relatively infrequently. The low probability of encountering a stimulus differing from a baseline or null stimulus condition in sparse stimulus sequences insures that gain control mechanisms within the nervous system will increase the neural response magnitude and also bias the measured responses to those neurone populations having such gain controls. The consequently increased response amplitudes ensure more reliably recorded responses than are obtained with non-sparse stimuli.

44 Claims, 7 Drawing Sheets

U.S. PATENT DOCUMENTS

| | | | | |
|---|---|---|---|---|
| 4,131,113 | A | * | 12/1978 | Fender et al. ................ 600/558 |
| 4,421,122 | A | * | 12/1983 | Duffy .......................... 600/544 |
| 4,832,480 | A | | 5/1989 | Kornacker et al. |
| 4,846,567 | A | * | 7/1989 | Sutter .......................... 351/224 |
| 5,522,386 | A | * | 6/1996 | Lerner ......................... 600/547 |
| 5,746,205 | A | * | 5/1998 | Virsu et al. .................. 600/544 |
| 6,022,107 | A | * | 2/2000 | Kutschbach et al. ........ 351/200 |
| 6,086,206 | A | * | 7/2000 | Sutter .......................... 351/224 |
| 6,315,414 | B1 | * | 11/2001 | Maddess et al. ............ 351/246 |
| 6,406,438 | B1 | * | 6/2002 | Thornton ..................... 600/559 |

FOREIGN PATENT DOCUMENTS

| | | |
|---|---|---|
| WO | WO 99/49776 | 10/1999 |

OTHER PUBLICATIONS

Bieser, et al., "Auditory responsive cortex in the squirrel monkey: neural responses to amplitude-modulated sounds" *Exp. Brain Res.* (1996) 108:273-284.

Boardman, et al., "Neural dynamics of perceptual order and context effects for variable-rate speech syllables" *Perception & Psychophysics.* (1999) 61(8):1477-1500.

Brooke, et al., "Mechanisms within the human spinal cord suppress fast reflexes to control the movement of the legs" *Brain Research.*(1995) 679:255-260.

Cain, et al., "The Effect of Sound Direction on Frequency Tuning in Mouse Inferior Collicular Neurons" *Chinese Journal of Physiology* (1999) 42(1):1-8.

Enroth-Cugell, et al., "The Contrast Sensitivity of Cat Retinal Ganglion Cells at Reduced Oxygen Tensions" *J. Physiol.* (1980) 304:59-81.

Klistomer, et al., "Multifocal Topographic Visual Evoked Potential: Improving Objective Detection of Local Visual Field Defects" *Investigative Ophthalmology & Visual Science* (1998) 39(6):937-950.

Kulikowski, "Relation of Psychophysics and Electrophysiology" *Trace* (1972) 6(1):64-69.

Leinonen, "Functional properties of neurones in the parietal retroinsular cortex in awake monkey" *Acta Physiol Scand* (1980) 108:381-384.

Maddess, et al., "Apparent fineness of stationary compound gratings" *Vision Research* (1999) 39:3404-3416.

Maddess, et al., "Evidence for spatial aliasing effects in the Y-like cells of the magnocellular visual pathway" *Vision Research* (1992) 38:1843-1859.

Victor, J. D., "The Dynamics of The Cat Retinal X Cell Centre" *J. Physiol.* (1987) 386:219-246.

Victor, J. D., "The Dynamics of The Cat Retinal Y Cell Subunit" *J. Physiol.* (1988) 405:289-320.

* cited by examiner

METHOD AND APPARATUS FOR ASSESSING NEURAL FUNCTION BY SPARSE STIMULI

CROSS-REFERENCE TO RELATED APPLICATIONS

This is the U.S. National Phase under 35 U.S.C. § 371 of International Application No. PCT/AU01/00343, filed Mar. 27, 2001, designating the United States and published in English, which claims priority to Australian Provisional Patent Application No. PQ 6465, filed Mar. 27, 2000.

FIELD OF THE INVENTION

This invention relates generally to assessment of neural function. More particularly, the present invention is concerned with a method and apparatus for assessment of neural function by temporally sparse stimuli with particular application to diseases affecting the sensory nervous system such as glaucoma, or diseases affecting nerve conduction such as multiple sclerosis.

BACKGROUND OF THE INVENTION

A conventional way to measure nervous system function is to record an evoked potential (EP) in response to a stimulus which is often presented repeatedly. The EP is a voltage representing the summed electrical activity of large number of neurones that reside near the recording electrodes. More recently, measurement of stimulus evoked responses (SERs) such as changes in magnetic fields or optical signals generated by neural activity have come into use. Another response generated by the nervous system providing possible utility is the pupillary response. Similarly the electroculogram, or eye movements measured in other ways, could be used. Such non-invasive measurement is desirable in the clinical setting and so neural activity is typically recorded from or through the skin in what might be described as surface recording. For example, evoked electrical potentials reflecting brain activity are easily recorded from electrodes placed upon the scalp. Magnetic and infrared signals related to neural activity can be similarly recorded through the skin. A potential drawback of surface measurements, or eye movements, or the pupillary response is that, however they are measured, these evoked responses typically represent the summed activity of many neurones in response to the stimulus.

Diseases affecting the nervous system may impact upon sections of the nervous system differentially. For example in the eye disease glaucoma separate parts of the retina are differentially affected causing localised reduction of visual performance in particular parts of the visual field. Like multiple sclerosis the damage caused by the disease is localised to small regions along the nerves and neural pathways within the brain. Thus, in such cases it would be useful to test neural function with multiple stimuli at the same time, each stimulus testing a different section of the nervous system, in what might be called Multi-stimulus Evoked Responses (MSERs). Measurement of MSERs to some extent minimises the difficulties of recording evoked responses. So, for example, stimuli presented to multiple parts of the visual field at the same time would in principle allow efficient mapping of the visual field even with a single recording sensor placed on or near the eye or scalp. Thus, the problems of recording evoked responses are reduced when responses to stimuli to multiple parts of the nervous system can be recorded.

While some MSER methods have been proposed, the emphasis in the design of the stimulus sequences used to date has been to reduce the computational burden in estimating the responses and/or to reduce the degree of correlation between the stimulus sequences. For example, Wiener, N ("Nonlinear problems in random theory", New York, Wiley, 1958) proposed the use of continuous Gaussian distributed white noise as a stimulus sequence that in principle could be used for MSERs. More recently Sutter, E (U.S. Pat. No. 4,846,567) proposed the use of special stimulus sequences called m-sequences where the stimulus sequence fluctuates between one of two levels in a strictly defined way. These two level m-sequences are a subset of a class of sequences that are said to be binary. These binary sequences vary between two about equally likely stimulus conditions and thus, unlike the stimuli proposed hereinafter, never contain a null condition and are not sparse in the sense presented herein. Neither of the stimuli of Wiener or Sutter is designed to optimise responses from any particular part of the nervous system. Stimuli that permit the measurement of MSERs but which are optimised for assessing clinically relevant parts of the nervous system would be potentially more useful.

Of particular interest in assessment of neural function may be those parts of the nervous system that dynamically adapt to prevailing stimulus conditions by using so called gain control mechanisms. These neural systems are interesting from the point of view of studying neural performance because these gain control systems are often complex and strictly controlled. Thus, neural dysfunction might be readily observed in neural systems exhibiting gain control mechanisms. At the same time appropriate design of stimulus sequences might permit neural systems with gain control systems to produce larger and or more reliable responses.

SUMMARY OF THE INVENTION

The present invention arises in part from the discovery that a low probability of encountering a stimulus differing from a baseline or null stimulus condition in sparse stimulus sequences as defined hereinafter insures that gain control mechanisms within the nervous system will increase the neural response magnitude and also bias the measured responses to those neurone populations having such gain controls. Sparse stimuli consist of temporal sequences of stimulus conditions presented against a baseline null stimulus condition, where the non-null stimulus condition, or conditions, are presented relatively infrequently. The consequently increased response amplitudes ensure more reliably recorded responses than are obtained with non-sparse stimuli. The inventors consider that biasing the response to those neural systems with gain controls will bias neural assessment to dynamic neural systems that are likely to become defective in disease.

The inventors have also discovered that even fairly short pseudorandom sparse stimulus sequences can be used to characterise the response of the nervous system by estimation of linear and non-linear weighting functions such as Wiener or Volterra kernels. Estimation of such kernels permits multiple stimulus sequences to be presented to the nervous system at the same time, and separate kernels to be estimated for each stimulus sequence. Simultaneous estimation of responses adds statistical power to the overall assessment process. It has also been surprisingly found that multiple stimuli such as, for example, ternary stimuli comprising a non-stimulus condition and two non-null stimulus conditions also permit separate and simultaneous estimates of kernels characterising responses to each of the non-null stimulus conditions within a ternary sequence. The inventors consider that such multiple stimuli, such as sparse ternary sequences consisting of infrequently presented bright and dark departures from a background null brightness level would be useful, for example, in testing for damage to those populations of visual neurones that respond separately to image points that are either darker or lighter than the average.

Thus, the prime objective of the present invention is the provision of a rapid reliable test for damage to the nervous system by measuring responses to multiple, simultaneously presented, stimuli, that appeal to gain control mechanisms of the nervous system, where such gain control mechanisms will enhance the responses to the stimuli and thus make the recorded responses more reliable. A preferred objective is to use stimuli that also permit isolation of responses from neurones that encode about half the sensory range as, for example, in the sets of visual neurones that encode information about parts of the visual field that are brighter or darker than average. Another objective of appealing to neural gain control mechanisms in the case of stimulation of the left and right sensory fields (e.g., to the left and right halves of the visual field) is to increase the symmetry of neural responses arising from the left and right sensory fields. All these objectives can be met by use of a particular class of stimuli termed sparse stimulus sequences.

Accordingly, in its broadest form, the invention provides a method for simultaneously assessing the functional status of component parts of the nervous system of a subject, said method comprising:

(a) presenting to one or more parts of the sensory nervous system of the subject stimulus sequences having different temporal modulation sequences of the appropriate stimulus modality for each stimulated part of the sensory nervous system, the stimuli having different sequences for each stimulated part;

(b) temporally modulating the stimuli between a null stimulus condition and at least one non-null stimulus condition selected from the group consisting of an increment stimulus condition and a decrement stimulus condition, relative to the null stimulus condition, wherein the probability of encountering the null stimulus condition in the stimulus sequences is higher compared to the probability of encountering the at least one non-null stimulus condition, and wherein the temporally modulated stimuli permit estimation of linear and non-linear weighting functions characterising measured responses to each stimulus presented to each part of the nervous system;

(c) estimating some or all of the coefficients of the linear and non-linear weighting functions for each stimulus sequence from the measured responses to said stimuli, to isolate separate responses from the separately and simultaneously stimulated component parts of the nervous system; and (d) estimating separate coefficients for responses to said other stimulus conditions to permit isolation of separate responses from component parts of the nervous system that respond to distinct members of said other stimulus conditions.

The non-null stimulus conditions include stimulation of a sensory modality. In a preferred embodiment of this type, the stimulation is selected from the group consisting of tactile stimuli, auditory stimuli and visual stimuli or a combination thereof.

The auditory stimuli may comprise different pressure levels or different tones. The tactile stimuli include any suitable somatosensory stimuli, including different pressure levels and different frequencies of a stimulus pressed against the skin or other tissues. The visual stimuli may comprise images of different brightness, whether actual or illusory, different luminance or contrast levels or modulations, different colours or colour contrasts, different patterns, textural densities or types, different pattern orientations or direction of movement, different image sizes, i.e., any valid modulation of the visual nervous system.

In a preferred embodiment, the stimulus sequence comprises a null stimulus condition and a number of non-null stimulus conditions wherein said non-null stimulus conditions are presented at a lower frequency relative to said null stimulus condition.

In another preferred embodiment, the stimulus sequence is characterised by a sparse bipolar stimulus sequence, preferably a sparse bipolar visual stimulus sequence, containing three stimulus conditions or levels, the null condition, being represented by a baseline condition, and two relatively infrequently presented non-null stimulus conditions that are increments and decrements of a parameter about the baseline condition. In this embodiment, the baseline condition suitably refers to a background stimulation level. For example, in the case of visual stimulation, the baseline condition may correspond to a background (or mean) luminance or brightness level.

In another preferred embodiment, the stimulus sequence is characterised by a sparse unipolar stimulus sequence containing a null stimulus condition and relatively infrequent occurrences of a non-null stimulus condition. For example, such a stimulus sequence may comprise a unipolar sparse visual stimulus sequence characterised by bright flashes only, which are presented relatively infrequently against a baseline brightness level.

Preferably, the step of presenting (step (a)) comprises:
dividing the visual field of view of each eye into a plurality of stimulus regions so as to roughly isolate confluent streams within the optic nerve, optic radiations and visual cortex due to their retinotopic arrangement and/or to stimulate different parts of areas of the brain concerned with vision; and
presenting to the two eyes stimuli having different temporal modulation of the appearance of each of the visual field of each eye, the stimuli being different for each of the corresponding regions within the visual field of view of each eye.

Preferably, the visual field is divided into quadrants partitioning the visual field along axes defining at least one member selected from the group consisting of the temporal, nasal, inferior and superior visual fields and concentrically organised partitions of these quadrants, which permits separate stimulation of central and peripheral parts of the visual field.

Preferably, in the above-preferred embodiment, the stimuli include modulation of the brightness or contrast of elements within each of the stimulus regions between two or three brightness levels or between two or three contrast levels.

Suitably, the temporally modulated stimuli are sufficiently complex so as to permit estimation of linear and non-linear weighting functions characterising the measured responses to each stimulus presented to each part of the nervous system.

Preferably, the stimulus sequences comprise aperiodic or pseudorandom stimulus sequences.

Preferably, the linear and non-linear weighting functions are Wiener or Volterra kernels.

Suitably, the latency to selected peaks within time course of linear kernels and/or the shape of the kernels or their amplitudes are used as measures of the functional status of component parts of the nervous system.

The non-null stimulus conditions within a stimulus sequence preferably occur with an average frequency of between about 0.25 and about 25 per second, more preferably between about 1 and about 6 per second. In an example of video stimulation at a frame rate of 50 Hertz this gives a probability of encountering the non-null stimulus of between about ½ and about ⅟₅₀.

In another aspect, the invention provides an apparatus for assessing the functional status of component parts of the nervous system, comprising:

stimulation means for presenting to the sensory nervous system of a test subject stimulus sequences having different temporal modulation sequences of the appropriate stimulus modality for each stimulated part of the sensory nervous system, the stimuli having different sequences for each stimulated part, wherein the stimulation means comprises means for fluctuating the temporally modulated stimuli between a null stimulus condition and at least one non-null stimulus condition selected from the group consisting of an increment stimulus condition and a decrement stimulus condition, relative to the null stimulus condition, wherein the probability of encountering the null stimulus condition in the stimulus sequences is higher compared to the probability of encountering the at least one non-null stimulus condition, and wherein the temporally modulated stimuli permit estimation of linear and non-linear weighting functions characterising measured responses to each stimulus presented to each part of the nervous system;

monitoring means for monitoring responses to said stimulus sequences in said test subject; and processing means for determining coefficients of linear and non-linear weighting functions for each stimulus sequence from the measured responses to said stimuli.

The stimulation means suitably comprises means for presenting a stream of separate, viewing images presented to each eye.

Suitably, the different viewing images comprise images of different contrast levels.

The monitoring means preferably comprises recordal means for recording responses to said stimulus sequences in said test subject.

Preferably, the recordal means records visual evoked potentials to provide an objective indication of the said responses.

The processing means suitably includes timing means and means for receiving signals from the recordal means indicative of said response.

DETAILED DESCRIPTION

Figure 1:
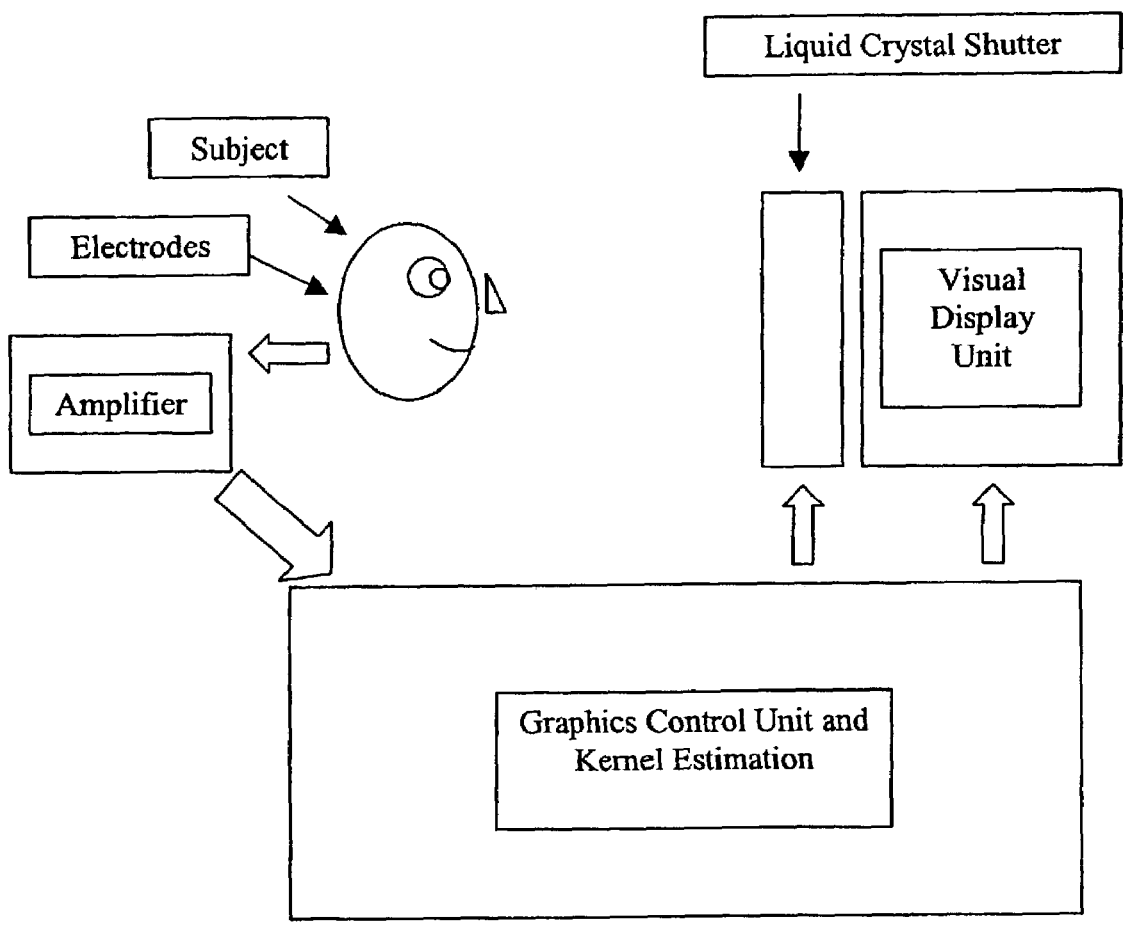
FIG. 1 is a functional block diagram of the basic system components forming a non-limiting embodiment of the apparatus of the invention for assessing the functional status of component parts of the nervous system.

Unless defined otherwise, all technical and scientific terms used herein have the same meaning as commonly understood by those of ordinary skill in the art to which the invention belongs. Although any methods and materials similar or equivalent to those described herein can be used in the practice or testing of the present invention, preferred methods and materials are described. For the purposes of the present invention, the following terms are defined below.

The articles "a" and "an" are used herein to refer to one or to more than one (i.e. to at least one) of the grammatical object of the article. By way of example, "an element" means one element or more than one element.

The term "about" is used herein to refer to frequencies or probabilities that vary by as much as 30%, preferably by as much as 20%, and more preferably by as much as 10% to a reference frequency or probability.

Throughout this specification, unless the context requires otherwise, the words "comprise", "comprises" and "comprising" will be understood to imply the inclusion of a stated step or element or group of steps or elements but not the exclusion of any other step or element or group of steps or elements.

The subject invention stems in part from the discovery that parts of the nervous system are controlled by mechanisms regulating their sensitivity and that some of these systems increase the response of the neurones they are regulating when stimuli appear infrequently compared to a baseline null stimulus condition. In this respect, the present inventors have found surprisingly that the low probability of encountering a stimulus differing from the baseline condition in sparse stimulus sequences insures that gain control mechanisms within the nervous system will increase the neural response magnitude and also bias the measured responses to those neurone populations having such gain controls. They have also found that sparse aperiodic stimulus sequences can be used to characterise these increased responses by means of computing linear and non-linear temporal weighting functions such as Wiener or Volterra kernels. The consequently increased response amplitudes ensure more reliably recorded responses than are obtained with non-sparse stimuli. Biasing the response to those neural systems with gain controls biases neural assessment to dynamic neural systems that are likely to become defective in disease. In the case of stimulation of both eyes simultaneously, for example, the biasing of the response towards neural systems dominated by gain controls increases the symmetries of responses obtained from the left and right visual fields compared to responses observed for more conventional dense stimuli such as binary stimulus sequences. Accordingly, the use of sparse stimulus sequences provides more reliable assessment of neural systems that are subject to gain controls. In this connection, glaucoma is known to be a disease affecting retinal neurones embodying a strong, rapid, contrast gain control. More generally, assessment of neural function will be enhanced further by the accurate measurement of the time evolution of neural responses afforded by this invention.

The inventors have reduced their discoveries to practice in a method and apparatus for simultaneously assessing the functional status of component parts of the nervous system as described more fully hereinafter. Briefly, the method involves measuring linear and non-linear temporal weighting functions known as kernels that characterise the linear and non-linear stimulus evoked responses of component parts of the nervous system. The method employs particular stimulus sequences that not only have a temporal structure that is sufficiently complex to permit calculation of the requisite kernels, but that also have properties causing gain control mechanisms within the nervous system to generate larger and more reliable neural responses. These same stimuli should also permit separate measurement of responses generated within the nervous system to those parts of the stimulus sequences containing stimuli that are increments above and/or decrements below the average stimulus level or strength.

While the method can be applied to stimulation of any sensory modality, such as tactile or auditory stimuli to isolate responses from regions of the nervous system where these different sensory modalities are encoded, the visual stimulation is preferred. This is because of the large number of neurones in the visual pathway and the relative case with which these many neurones can be stimulated by the presentation of images to the eye. As well, the visual system produces observable stimulus evoked responses in the form of the pupil size and oculomotor activity.

Not wishing to be bound by any one particular theory, the reasoning that led to the development of the present invention is provided below.

As noted above Multi-stimulus Evoked Responses (MSERs) would likely be enhanced if the stimuli used would cause gain control mechanisms to enhance the reliability of the responses recorded. Also the clinical relevance of the recorded signals would be enhanced if recorded responses were biased towards those neural systems having such gain control mechanisms because neurological disease is likely to affect these gain control systems.

The visual nervous system is of particular interest because each optic nerve contains about one million nerve fibres and the majority of the brain is concerned with processing visual input. The visual inputs that carry information about luminance contrast in each part of the retinal image have a strong, rapidly acting gain control system as discussed in the paper by Benardete, E. A., et al, 1992, *Vis Neurosci*. 8(5): 483–486, entitled "Contrast gain control in the primate retina: P cells are not X-like, some M cells are". As discussed by those authors, this gain control system is manifested in retinal ganglion cells that project to the magnocellular layers of the dorsal lateral geniculate nucleus (dLGN), these retinal ganglion cells are thus referred to as M-cells. M-cells come in at least two varieties: the relatively more linearly responding MX-cells, and the more non-linearly responding MY-cells. The retinal gain control system acts so that responses to novel, visually large scale, stimuli are enhanced. Thus, in response to a step change in contrast over time, the neural response of the M-cells to the initial transient change is amplified and the response to the extended plateau part of the stop change in contrast diminishes rapidly in time as shown in the papers by J. D. Victor, entitled "The dynamics of the cat retinal Y cell subunit" (1988, *J Physiol.* (*Lond*). 405: 289–320), and "The dynamics of the cat retinal. X cell centre" (1987, *J Physiol* (*Lond*). 386: 219–246). The response to a single brief change in contrast is similarly enhanced. Such a single brief change in contrast which is too fast for a system to respond to anything more than the total time integrated energy of the stimulus is sometimes described as an impulsive stimulus. Such mechanisms may explain the enhancement of image contrast observed visually and in evoked potential, amplitudes in response to infrequently but periodically presented grating patterns as discussed by Kulikowski, J. J. ("Relation of psychophysics to, electrophysiology" *Trace* (*Paris*), 6: 64–69). Such periodic stimuli could not, however, be used to estimate Wiener or Volterra kernels.

Evidence has been presented for somewhat similar gain control mechanisms operating in other sensory modalities such as the somatosensory system by Brooke, J. D., et al. (1995, "Mechanisms within the human spinal cord suppress fast reflexes to control the movement of the legs", *Brain Research* 679: 255–260) and in the auditory nervous system by Boardman, I., et al. (1999, "Neural dynamics of perceptual order and context effects for variable-rate speech syllables." *Percept Psychophys.* 61(8): 1477–1500).

In the visual system the M-type retinal ganglion cells can be placed into a relative high gain state by the frequency domain equivalent of a brief stimulus a continuous high frequency modulation of the contrast. One such example is that of the use of the spatial frequency doubling illusion for the diagnosis of glaucoma as discussed by James, A. C. and Maddess, T. in Australian Patent, No. 667,702 entitled "Glaucoma testing using non-linear systems identification techniques", by Maddess, T. in Australian Patent No. 611, 585 entitled "Method and apparatus for use in diagnosis of glaucoma", and by Maddess, T. L. in Australian Patent No. 701,075 entitled "Early detection of glaucoma". The spatial frequency doubling illusion is an illusory visual percept that is seen when periodic grating patterns, having low spatial frequencies, have their contrast modulated, rapidly in time at a fixed high frequency, typically faster than 15 Hz. Under these conditions subjects report the periodic grating patterns as having twice as many stripes as are actually present, hence the name spatial frequency doubling (FD) illusion.

The above patent documents hypothesise that the illusion is the product of a highly excited gain control mechanism expressed in the above mentioned non-linear MY retinal ganglion cells. A disadvantage of those methods is that such frequency domain methods provide information about the response of the nervous system to a single frequency. Also, visual mechanisms residing at the level of the visual cortex can interfere with persons ability to see the true FD effect produced by the retina (Maddess T. and Kulikowski, J. J., 1999, "Apparent fineness of stationary compound gratings" *Vision Res.* 39(20): 3404–16). Time domain tests would in principle provide a broader assessment of the nervous system since it will be understood by a person skilled in the art that such stimuli are effectively stimulating the nervous system with many frequencies at once and also permit estimation of the stimulus to response delay interval. The current method offers a way to measure MSERs with time, domain stimuli that, like the FD methods mentioned above, cause gain control mechanisms to provide enhanced neural responses. In addition the stimuli and method proposed provides other benefits in terms of reducing the variability of the evoked responses and enhancing their applicability for clinical assessment of the nervous system.

The convoluted surface of the cerebral cortex and other brain areas presents a problem when measuring SERs from the scalp in response to any type of sensory stimulus. The folding of these brain structures means that the electrical currents arising from brain activity sum together spatially so that signals available to be measured as surface potentials may be spatially distorted or uneven. In the visual system this translates into falsely distorted MSERs that do not accurately reflect the level of retinal responses in different parts of the retina as discussed in the paper by Klistorner, A., et al. (1988, "Multifocal topographic visual evoked potential: improving objective detection of local visual field defects" *Invest Ophthalmol Vis Sci.* 39(6): 937–950). Those authors attempted to ameliorate the problems caused by cortical folding by placing multiple electrodes on the scalp in a particular spatial configuration.

The left and right halves of the brain typically process sensory signals from their respective opposite sides of the body, although some overlap occurs, notably in the visual cortex, where neurones from the left and right eyes converge to produce binocular vision. It is worth noting that this convergence only serves to have binocular information about the right half of the visual field processed by the left visual cortex, and likewise, binocular information from the left half of the visual field processed by the right visual cortex. In a similar way maps of the somatosensory input from the body, and the auditory input from the world are present in different brain areas. Our ability to discern the details of the sensory input from surface recordings from these areas will be similarly affected by brain folding. The left and right halves of the brain are most often not folded in the same way and the naso-caudal mid-line of the brain may not always be precisely aligned with the mid-line of the head. Thus, brain folding and brain position within the head can potentially create left-right asymmetries in surface recordings from all sensory input to the two, halves of the visual field, ears or sides of the body. Obviously, all such distortions will limit the value of surface recordings, particularly MSERs, where one is attempting to distinguish responses from different component parts of the nervous system.

A possible method for partly resolving these asymmetries and distortions may arise from studying gain control mechanisms. In work leading up to the present invention, Maddess, T., et al (1998, "Evidence for spatial aliasing effects in the Y-like cells of the magnocellular visual pathway" *Vision Res.* 38(12): 1843–1859) have shown that neurones relaying signals about retinal gain control mechanisms to the brain can be relatively sparse without compromising their function. In the case of MX and MY retinal ganglion cells a single gain control mechanism regulates the activity of both kinds of cells but only the less numerous MY-cells convey information about the gain control process to the brain. The more numerous MX-cells sample the retinal image densely, and the MY-cells sample the retinal image less densely. The authors showed that even though there are fewer MY-cells this might not compromise the brain's ability to understand what is happening to the gain of the more numerous MX cells. This economy of gain control encoding neurones is allowed if the gain control mechanism is based on measures of neural activity related to what engineers refer to as power. Each nerve fibre imposes a metabolic cost on the body so evolution will adopt mechanisms that insure tile minimum number of nerve fibres that permits the nervous system to operate accurately. Thus, it is likely that many sensory mechanisms have similar economics in the number of neurones conveying information about gain control.

The relevance of this potential sparsity of nerve cells conveying gain control information around the nervous system is that, on the large brain areas were sensory information is represented as a largely contiguous map of the sensory input from the world, the gain control neurones will be sparsely spread across these maps. In this regard, Maddess, T., et al. (1998, *Vision Res.* 38(12): 1843–1859) have provided evidence that there are perhaps only 1 or 2 MY-cell inputs per cytochrome oxidase blob, a unit part of the visual cortex covering about a square millimetre of visual cortical surface in the human MX-cells may be of more direct interest in the present application but there are only about 5 to 10 times more of those neurones than MY-cells. Each MY-cell carries information about the gain of several MX-cells so cortical interpretation of gain changes to MX-cells may be organised with a sparseness comparable to MY-cell densities. These sparse arrays of neurones projected onto the cortex will, by definition, be unable to provide an accurate spatial representation of intricate brain foldings. As indicated by the above authors basic sampling theory tells us that providing the position of the gain control affected neurones is spatially random across the brain mapping the information arising from detailed brain foldings will be scattered into broad band noise, and thus have no average effect on the position of summed neural activity. This would lead to smaller effects of brain folding upon SERs measured from such cells. Similarly, left right asymmetries may also be reduced as the differential folding of the left and right halves of the brain may be of less impact.

Another way to enhance the applicability of stimuli for clinical assessment of the nervous system would be the ability to separately assess the response of the nervous system to stimuli that are either increments above or decrements below a continuous null stimulus. This is because separate classes of neurones within the nervous system are known to respond to either stimulus increments or decrements. In the visual nervous system groups of neurones responding separately to either increments or decrements of image brightness are well known as exemplified by Enroth-Cugell C., et al. (1980, "The contrast sensitivity of retinal ganglion cells of the cat" *J Physiol (Lond).* 304: 59–81). Cells responding to brightness increments are referred to as ON-units while those responding to brightness decrements are referred to as OFF-units. The previously mentioned MX and MY retinal ganglion cells come in ON and OFF classes.

The characteristic non-linear response component of MY-cells makes them respond in part to increments or decrements about equally, such a response quality being referred to as ON-OFF. This ON-OFF character is related to the gain control signal these neurones carry as discussed by Victor, J. D. (1988, supra) and so ON-OFF responses may in general reflect the presence of similar gain control mechanisms. This ON-OFF response quality is amenable to quantification by second order Wiener Volterra or similar kernels perhaps permitting more direct assessment of the operating condition of neural gain control systems. ON, OFF and ON-OFF responses to increments and decrements in stimulus strength are common features of the neurones of sensory nervous system for example being reported for neurones of the auditory nervous system by Cain, D. et al. (1999, "The effect of sound direction on frequency tuning in mouse inferior collicular neurones", *Chin J Physiol.* 42(1): 1–8) and Bieser, A. et al. (1996, "Auditory responsive cortex in the squirrel monkey: neural responses to amplitude-modulated sounds" *Exp Brain Res.* 108(2): 273–84), and somatosensory brain by Leinonen, L. (1980, "Functional properties of neurones in the parietal retroinsular cortex in awake monkey", *Acta Physiol Scand.* 108(4): 381–4).

An efficient way to characterise the response of neurones is through the estimation of linear and non-linear weighting temporal functions known as kernels. These kernels can summarise linear response of the system under study and also non-linear interactions in the response. Multiple stimuli can be presented simultaneously and the responses to each characterised by separate kernels for each stimulus. For example, the present inventors in WO 99/49776 describe a method for estimating binocular interaction kernels and their potential use in diagnosing and monitoring diseases like multiple sclerosis.

From the foregoing, the present inventors considered that stimuli which could simultaneously be used to estimate kernels, and which caused neural gain control processes to enhance responses, and which permitted separate assessment of responses to stimuli containing increment and/or decrement stimuli from a prevailing baseline stimulus, and which might minimise the effects of brain folding, would provide efficient, non-invasive, assessment of broad sections of the nervous system.

Given the above the present inventors hypothesised that stimuli consisting of pseudorandom temporal, sequences consisting of a null stimulus condition, and other stimulus conditions representing increments or decrements from the null stimulus condition, and where the probability of encountering stimulus levels or qualities other than the baseline null stimulus condition was relatively low would provide the following:

(a) The temporally sparse nature of the increment and/or decrement stimuli would cause neural gain control mechanisms to enhance responses of those neural systems having such controls, much as single impulsive or step stimuli excite these mechanisms;

(b) The recorded responses arising from neural activity being biased towards such gain control mechanisms would thus bias the observed response towards mechanisms likely to be compromised by disease, (c) The pseudorandom occurrence of the increments and decrements would make the stimuli sufficiently statistically rich as to permit the estimation of kernels in response to multiple stimuli thus making MSERs possible, even for quite short stimulus sequences;

(d) The presence of increments and decrements above and below the prevailing baseline stimulus condition would permit estimation of separate kernels for increment and decrement stimuli and to permit isolation of the separate responses of those neural mechanisms responding separately to increments and decrements.

In order that the invention may be readily understood and put into practical effect, particular preferred embodiments will now be described by way of the following non-limiting examples.

EXAMPLES

Example 1

Apparatus

A schematic of the basic system components forming an embodiment of the apparatus of the present invention is shown in FIG. 1. The major components are an apparatus for dichoptic stimulation of the two eyes, in the present non-limiting example by means of a liquid crystal shutter, a means for assessing cortical neural responses, in the present example electrodes, an amplifier for recording a visual evoked electrical potential, and a means for computing estimates of kernel coefficients. Thin arrows associate labels with objects while thick block arrows indicate the direction of information flow or control.

The test stimuli for each subject were presented on a video monitor at 101 pictures per second. Since the stimuli were presented on a video monitor it is common to refer to the sequence of pictures presented as a sequence of frames presented at a particular frame rate, in this case 101 frames per second. The stimulus sequence consisted of a stream of separate, but temporally interleaved, images presented alternately to each eye at 50.5 frames per second by use of a liquid crystal shutter. Presentation of separate images to the two eyes is referred to as dichoptic presentation. To achieve dichoptic presentation of the stimuli to the two eyes the liquid crystal shutter transmitted on alternate frames, light that is left or right circularly polarised, the changes in polarisation being synchronised to the picture presentation rate of 101 frames per second. Subjects wore glasses where the element covering each eye transmitted only one of the two polarisations of the light transmitted through the shutter. In this way each eye saw only one of the two interleaved video sequences, each eye receiving pictures at 50.5 frames per second. Subjects also wore normal corrective lenses as necessary. The total duration of the test sequences was 40 seconds and up to 8 sequences were presented to each subject.

Subjects were asked to fixate a spot presented at the centre of the visual stimulus. Persons skilled in the art will recognise that other means of maintaining fixation, such as monitoring eye position could have been substituted without affecting the present demonstration. Evoked potentials were recorded with the samples being obtained synchronously with the rate of presentation of video stimuli. Faster sampling rates could have been used but for the present demonstration four sample per frame was used. Standard gold cup electrodes were placed on the scalp to record the evoked potentials. The dichoptic stimulus generation scheme and the VEP recording apparatus are illustrated in FIG. 1. However, it should be noted that the present invention is not predicated on the use of any one particular means of recording evoked neuronal responses. In this regard, persons of skill in the art will recognise that evoked neuronal responses may be recorded by means other than be measuring electrical potentials such as by recording changes in magnetic, or electromagnetic radiation, or acoustic signals.

Example 2

Pseudorandom Stimulus Sequences

Figure 2:
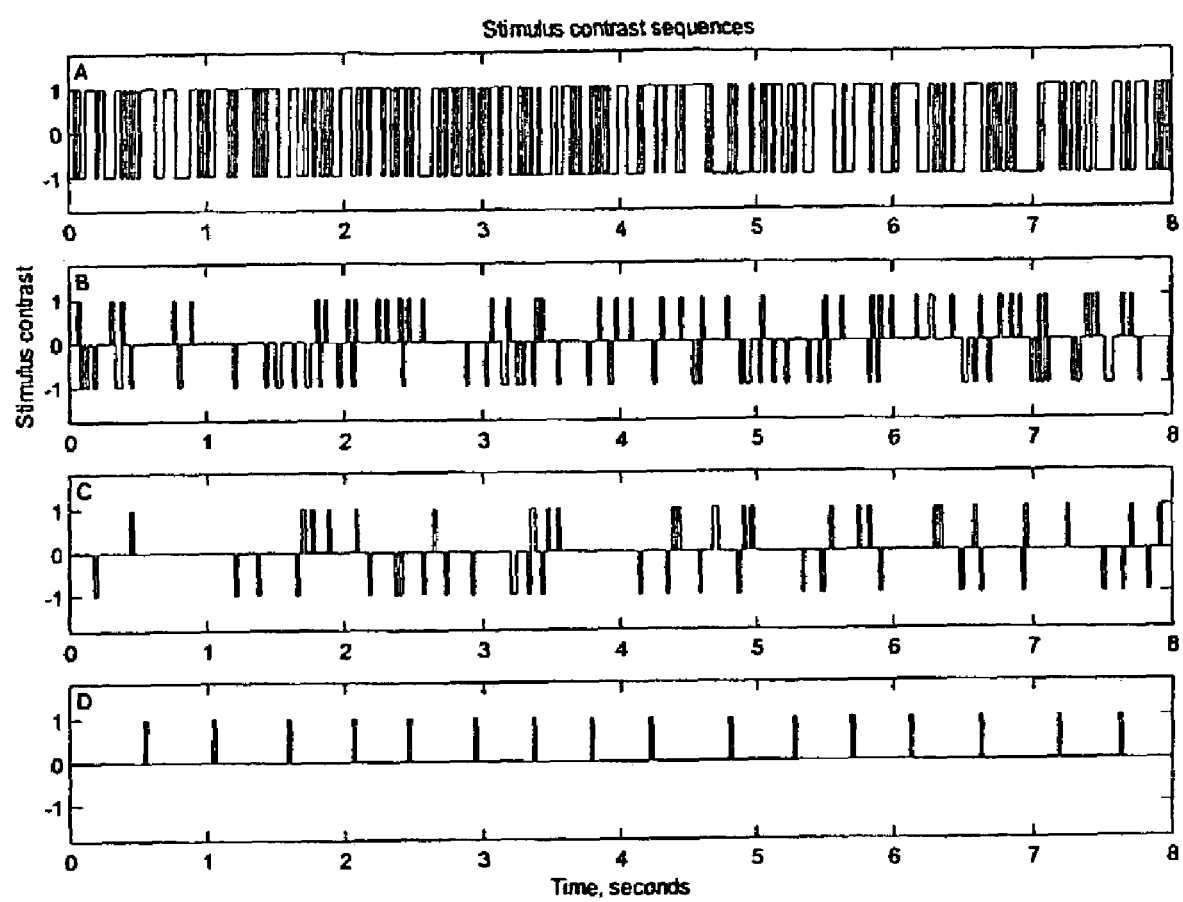
FIG. 2 illustrates four types of pseudorandom stimulus sequences. The upper panel illustrates a binary sequence where the stimulus varies between two levels. The central panel illustrates a ternary or bipolar version of a sparse pseudorandom stimulus sequence. In this instance, the stimulus has three levels including a more frequent null stimulus condition, at the middle stimulus level, and two less frequent stimulus conditions, at levels above and below the null stimulus condition. The third panel illustrates a more sparse ternary pseudorandom stimulus sequence. The fourth panel illustrates a unipolar very sparse pseudorandom stimulus sequence consisting of a unipolar non-null stimulus condition presented with randomly distributed interstimulus interval.

The relevant feature of the sparse nature of the pseudorandom stimulus sequences will be better understood by inspection of FIG. 2, which illustrates 4 types of pseudorandom stimulus sequences. The upper panel (A) illustrates a binary sequence where the stimulus varies between two levels. The stimulus was generated with a pseudorandom number generator with an even distribution and the probability of the stimulus being in either stimulus condition at a given time step was set to ½. Thus, the frequency of non-null stimulation was ½(50.5), equal to 25.25 pattern reversals per second per eye. The second panel (B) illustrates a ternary or bipolar version of a sparse pseudorandom stimulus sequence. Here the stimulus has three levels including a more frequent null stimulus condition, at the middle stimulus level, and two less frequent stimulus conditions, at levels above and below the null stimulus condition. In this case the probability of encountering the null condition was set to ½ and that of the other two states was set to ¼. Thus, the frequency of non-null stimulation was (¼+¼) (50.5), equal to 25.25 pulsed stimuli per second per eye. The third panel (C) illustrates a more sparse ternary pseudorandom stimulus sequence where the probability of the null state was set to $^{14}/_{16}$ and of encountering the other two states was $^{1}/_{16}$. Thus, the frequency of non-null stimulation was ($^{1}/_{16}$+$^{1}/_{16}$) (50.5), equal to 6.31 pulsed stimuli per second per eye. It should be noted that the particular examples are eight-second sections of the actual 40-second stimulus and so the probabilities exhibited may not reflect those of the generating random process. The fourth panel (D) illustrates a unipolar very sparse stimulus sequence in which a single type of non-null stimulus condition is presented infrequently, with an interstimulus interval being always above a minimum value, chosen to be above the duration of response to the stimulus condition. This lowest panel (D) represents a preferred but non-limiting embodiment of a sparse sequence. The stimulus sequences might just as well describe auditory stimuli where the stimulus conditions correspond to changes in sound pressure or frequency. Similarly the sequences might describe somatosensory stimuli such as changes in pressure level or frequency of a stimulus pressed against the skin or other tissue. The sparseness of the stimulus sequences would be appropriate to the modality stimulated. The stimulus sequences also do not have to have sharp rectangular transitions as shown in FIG. 2 but may be smoothed in various ways and the temporal evolution of the departures from the null stimulus may be different for different non-null stimuli.

Example 3

Visual Stimulus

Figure 3:
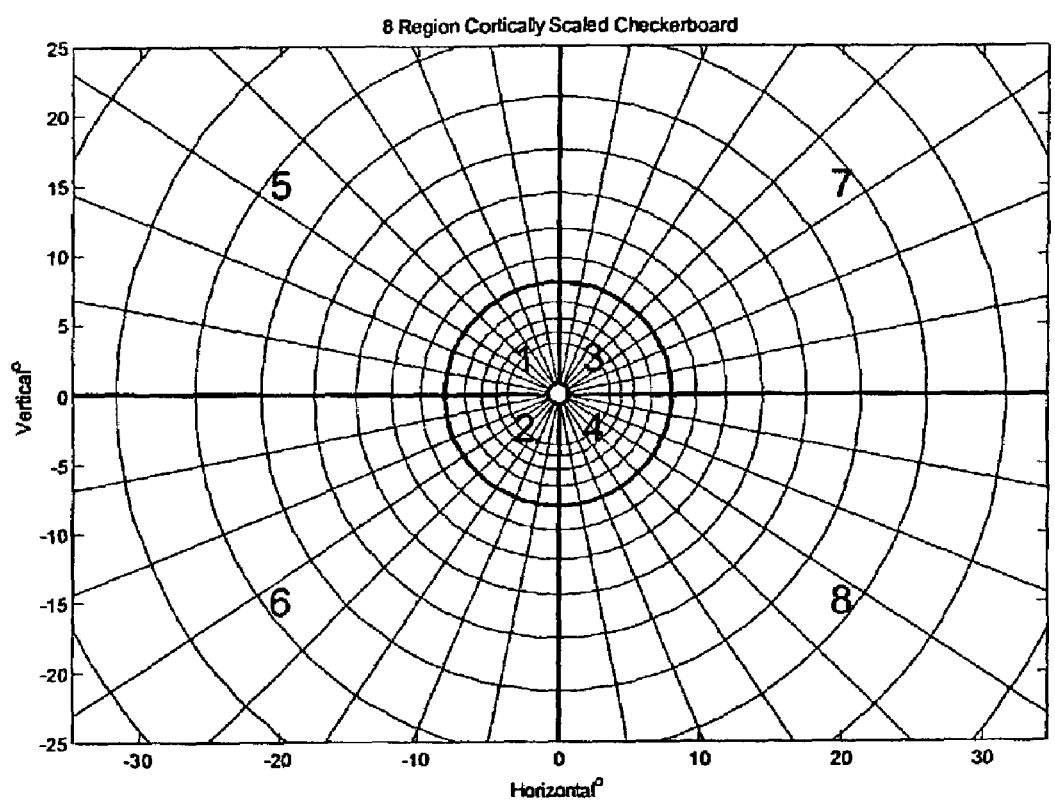
FIG. 3 shows a schematic representation of the spatial layout of the visual stimulus used in a non-limiting embodiment of the apparatus of the invention.

FIG. 3 illustrates a visual stimulus for a particular non-limiting embodiment in which the face of a video monitor was divided into 8 parts demarked by the bold lines. In the tests described in the figures that follow subjects observed visual stimuli presented in each of the 8 regions and evoked potentials were recorded. The numbers in each of the eight regions shown will be used in the subsequent 3 figures to refer to these regions. Black and white checkerboard patterns were presented within each region, the boundaries of the checks being shown by the thin lines. Each region had its contrast modulated in time by different pseudorandom sequences each 40 s long. For the binary sequences of FIG. 2 white checks are considered to have contrast 1 and black checks contrast −1. Thus the temporal modulation sequences caused the checks within each of the 8 regions to flip the sign of their contrast or remain the same contrast according to the state, 1 or −1, of the binary sequence at a given time step. For ternary stimuli the null stimulus condition for each of the regions was a uniform mid-level grey luminance, defined as having contrast zero; one of the non-null conditions had alternate black and white checks as in a checkerboard, defined as contrast 1; the other non-null condition reversed the contrast of the checks, white interchanging with black, and was defined as contrast level −1. The eight regions for each of the two eyes were modulated simultaneously in contrast according to independent stimulus sequences. In separate recordings the three types of stimulus sequences illustrated in FIG. 2 were used and in each case Wiener kernels were estimated from the evoked potentials.

Example 4

Pseudorandom Binary Sequence A

Figure 4:
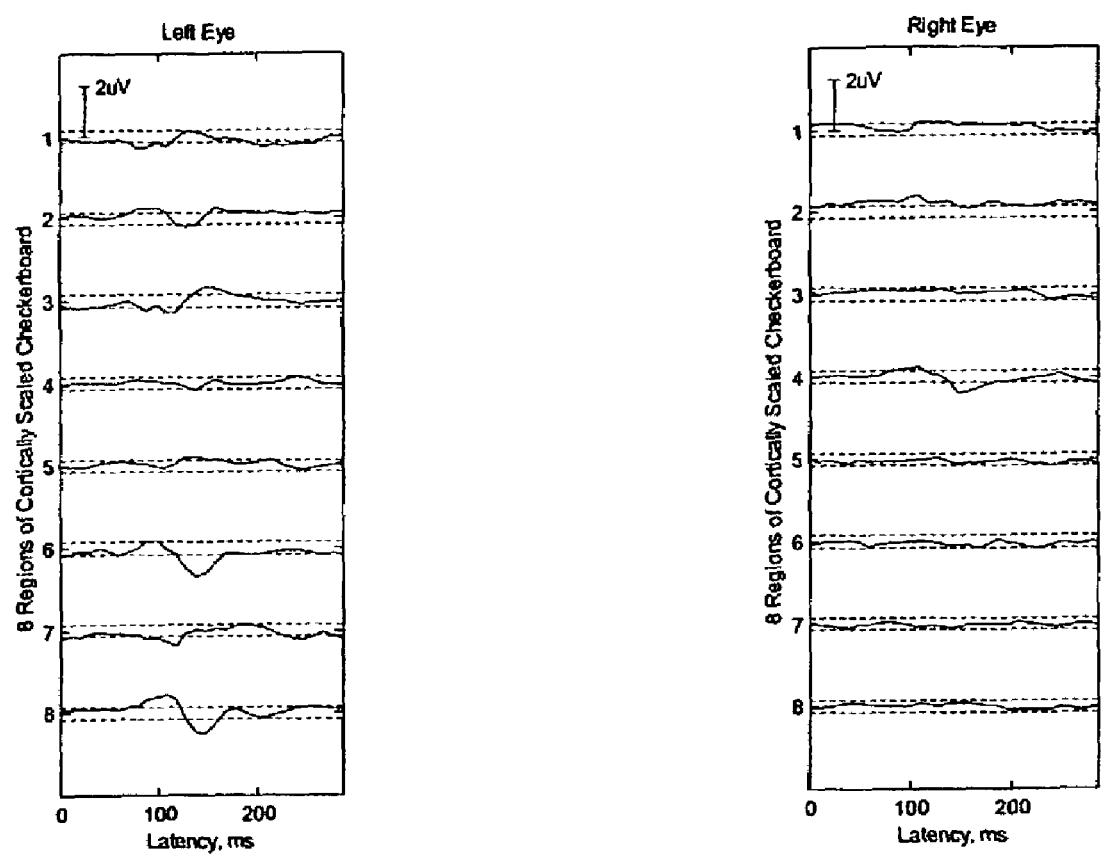
FIG. 4 shows Wiener kernel coefficients estimated for each of the eight regions of FIG. 3. The left panel represents kernels from the 8 regions of FIG. 3 when presented to the left eye. The right panel represents kernels obtained when the stimulus presentation was to the right eye.

With reference to FIG. 4, the stimuli were pseudorandom binary sequences as shown in panel A of FIG. 2. The left column represents kernels from the 8 regions of FIG. 3 when presented to the left eye. The right column represents kernels obtained when the stimulus presentation was to the right eye. Each of the eight curves is the first off-diagonal of the second order self-quadratic Wiener kernel. The values of all points in all kernels are presented as voltage response, in units of microvolts as indicated by the scalebars. The pair of horizontal dotted lines for each kernel represents plus and minus 1.96 times the estimated standard error of the kernel, giving the critical region for a test of significance of the kernel values at the ±95% confidence level. Thus, parts of the kernels that occur above or below these dotted lines are significant at the 95% level or better. The subject was a 20 year old female; kernels are calculated from eight repetitions of a 40 second stimulus. It should be noted that many of the quadratic kernels are not significant and that there is considerable difference in the kernels obtained for the left and right eyes.

Example 5

Pseudorandom Bipolar Sequence B

Figure 5:
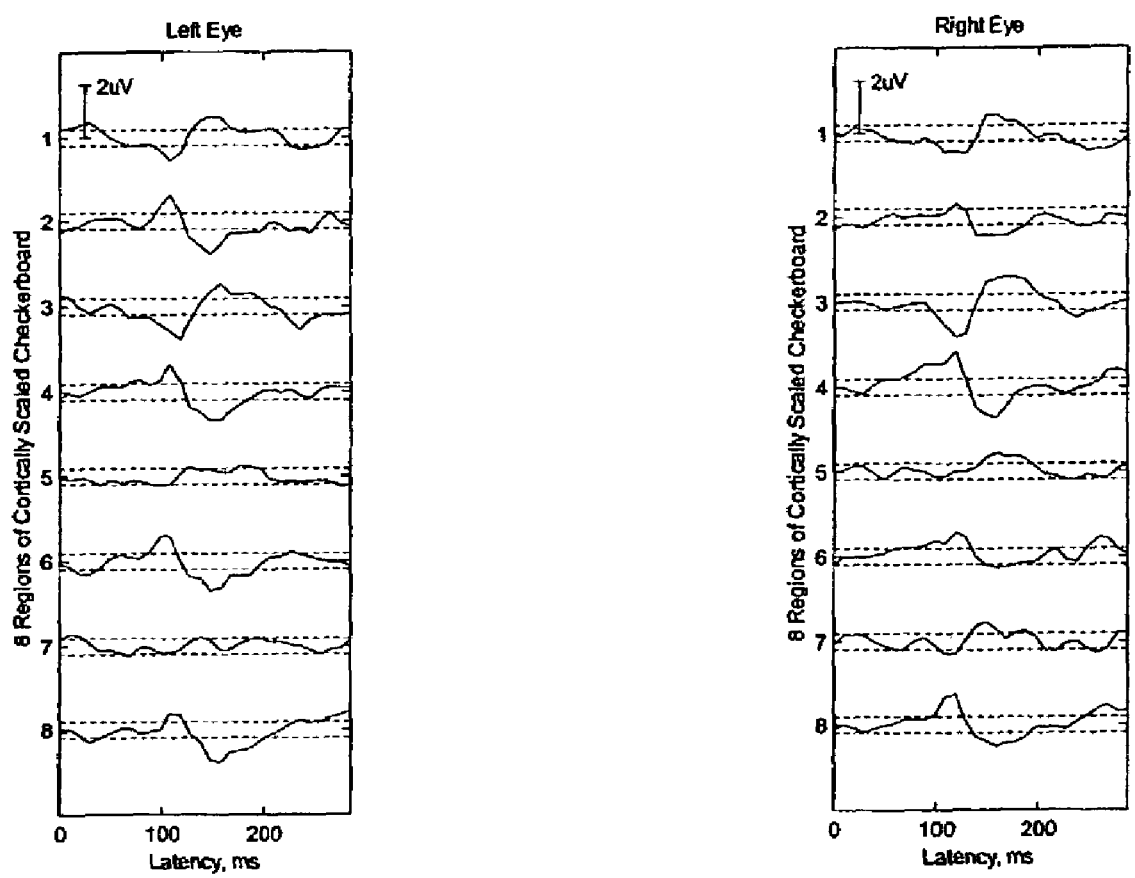
FIG. 5 is similar to FIG. 4 except that the stimulus sequence was a sparse sequence of the type illustrated in the central panel of FIG. 2 where the probability of generating the null stimulus condition was ½ and the probability of generating each of the other two conditions was ¼ each. The conventions are otherwise as in FIG. 4.

FIG. 5 shows similar information to FIG. 4 but the stimulus sequence was a sparse sequence of the type illustrated in panel B of FIG. 2 where the probability of generating the null stimulus condition was ½ and the probability of generating each of the other two conditions was ¼ each. Thus, the frequency of non-null stimulation was (¼+¼) (50.5), equal to 25.25 pulsed stimuli per second per eye. The conventions are otherwise as in FIG. 4. The data is from the same subject obtained in with the recordings interleaved between those that generated FIGS. 3 and 5. Notice that more of the kernels are significant than in FIG. 4 and that the kernels from the two eyes are more similar than in FIGS. 3.

Example 6

Pseudorandom Bipolar Sequence C

Figure 6:
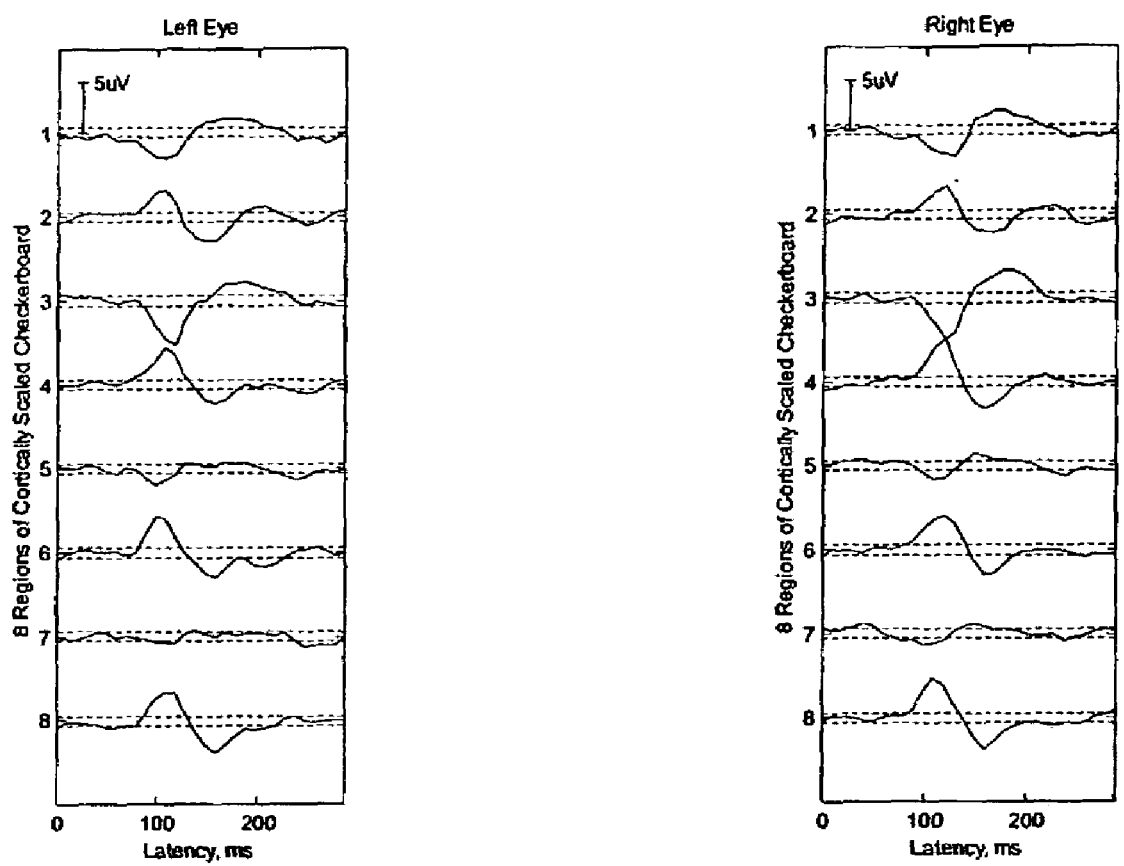
FIG. 6 is similar to FIGS. 3 and 4 except that the stimulus sequence is a sparse sequence of the type illustrated in the third panel of FIG. 2 where the probability of generating the null stimulus condition was ¹⁴⁄₁₆ and the probability of generating each of the other two conditions was ⅟₁₆ each. The conventions are otherwise as in FIG. 4.

FIG. 6 shows similar information to FIGS. 3 and 4 but the stimulus sequence is a sparse sequence of the type illustrated in panel C of FIG. 2 where the probability of generating the null stimulus condition was $^{14}/_{16}$ and the probability of generating each of the other two conditions was $^{1}/_{16}$ each. Thus, the frequency of non-null stimulation was ($^{1}/_{16}$+$^{1}/_{16}$) (50.5), equal to 6.31 pulsed stimuli per second per eye. The conventions are otherwise as in FIG. 4. The data is from the same subject obtained in recordings interleaved between those that generated FIGS. 4 and 5. It should be noted that more of the quadratic kernels are significant than in either FIG. 4 or 5 and that the kernels from the two eyes are more similar than in either FIG. 4 or 5. Thus, as the stimulus sequences become steadily more sparse the reliability of the kernels increases.

Example 7

Pseudorandom Unipolar Sequence D

Figure 7:
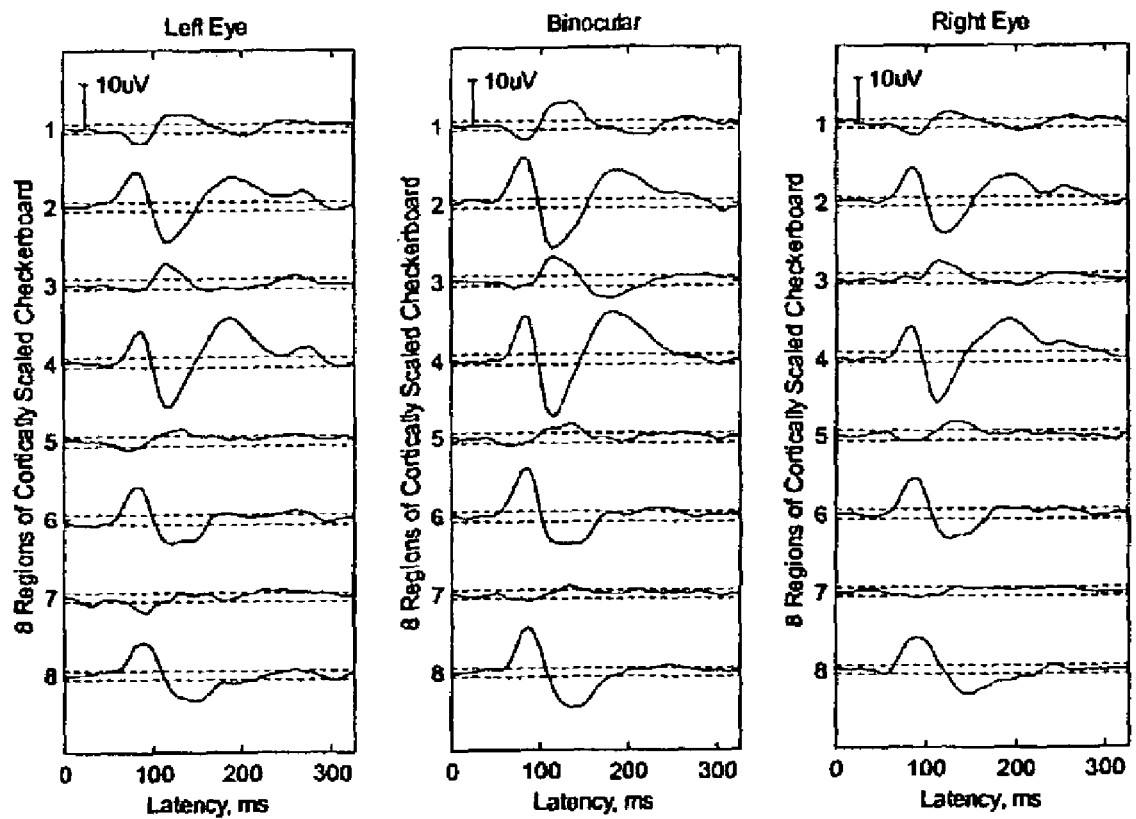
FIG. 7 is similar to FIGS. 3, 4 and 5 except that the stimulus sequence is a unipolar very sparse sequence of the type illustrated in the lower panel of FIG. 2 where the interstimulus interval was randomly distributed between 0.4 and 0.6 seconds. The conventions for left and right panels are otherwise as in FIG. 4, that is, for presentation of the non-null stimulus to left and right eye respectively. The central panel illustrates Wiener kernels for presentation of the non-null stimulus condition to both eyes, that is, binocular presentation.

FIG. 7 shows similar information to FIGS. 4, 5 and 6 but the stimulus sequence is a unipolar very sparse sequence of the type illustrated in panel D of FIG. 2 where one non-null stimulus condition is presented repeatedly with an interstimulus interval distributed randomly between 0.4 and 0.6 seconds, thereby providing an average interstimulus interval of 0.5 seconds, which corresponds to a stimulus frequency of 2.0 per second. Because the stimuli are presented in alternate frames seen by only one of the two eyes, there is an average of 1.0 stimulus/second/eye. The kernels plotted are the estimated first-order Wiener kernels, in units of microvolts as indicated by the scalebars. Dashed horizontal lines are drawn at plus and minus 1.96 times the estimated kernel standard errors, thus giving the critical region for a test of significance at the 95% confidence level. The data is from a 45-year-old female; kernels are calculated from 4 repeats of a 40-second stimulus sequence. In this figure left and right panels illustrate kernels pertaining to stimuli presented to left and right eyes respectively. The central panel illustrates kernels pertaining to presentation to both eyes, that is binocular presentation. Notice that large amplitude, highly significant kernels can be obtained from all regions, and from left eye, right eye and binocular presentation, all from a total of 4 times 40 seconds, that is 160 seconds of total recording time.

The disclosure of every patent, patent application, and publication cited herein is incorporated herein by reference in its entirety.

The citation of any reference herein should not be construed as an admission that such reference is available as "Prior Art" to the instant application Throughout the specification the aim has been to describe the preferred embodiments of the invention without limiting the invention to any one embodiment or specific collection of features. Those of skill in the art will therefore appreciate that, in light of the instant disclosure, various modifications and changes can be made in the particular embodiments exemplified without departing from the scope of the present invention. All such modifications and changes are intended to be included within the scope of the appendant claims.

What is claimed is:

1. A method for simultaneously assessing the functional status of component parts of the nervous system of a subject, said method comprising:

(a) presenting to one or more parts of the sensory nervous system of the subject stimulus sequences having different temporal modulation sequences of the appropriate stimulus modality for each stimulated part of the sensory nervous system, the stimuli having different sequences for each stimulated part;

(b) temporally modulating the stimuli between a null stimulus condition and at least one non-null stimulus condition selected from the group consisting of an increment stimulus condition and a decrement stimulus condition, relative to the null stimulus condition, wherein the probability of encountering the null stimulus condition in the stimulus sequences is higher compared to the probability of encountering at least one non-null stimulus condition, and wherein the temporally modulated stimuli permit estimation of linear and non-linear weighting functions characterising measured responses to each stimulus presented to each part of the nervous system, wherein the at least one non-null condition occurs with an average frequency of between about 0.25 Hz and about 6 Hz;

(c) estimating some or all of the coefficients of the linear and non-linear weighting functions for each stimulus sequence from the measured responses to said stimuli, to isolate separate responses from the separately and simultaneously stimulated component parts of the nervous system.

2. The method of claim 1, wherein a stimulus sequence comprises a null stimulus condition and two non-null stimulus conditions comprising an increment stimulus condition characterised by an increment of a parameter relative to the null stimulus condition, and a decrement stimulus condition characterised by a decrement of a parameter relative to the null stimulus condition, wherein said non-null stimulus conditions are presented at a lower frequency relative to said null stimulus condition.

3. The method of claim 1, wherein a stimulus sequence comprises a null stimulus condition and a single non-null stimulus condition, wherein said non-null stimulus condition is presented at a lower frequency relative to said null stimulus condition.

4. The method of claim 1, wherein a stimulus sequence comprises a null stimulus condition and a number of non-null stimulus conditions wherein said non-null stimulus conditions are presented at a lower frequency relative to said null stimulus condition.

5. The method of claim 1, wherein the at least one non-null condition occurs with an average frequency of between about 1 and about 6 per second.

6. The method of claim 5, wherein the stimulation is selected from tactile stimuli, auditory stimuli, visual stimuli or a combination thereof.

7. The method of claim 1, wherein the at least one non-null condition comprises stimulation by visual stimuli.

8. The method of claim 7, wherein the visual stimuli are selected from different luminance or contrast levels.

9. The method of claim 7, wherein a stimulus sequence comprises a null stimulus condition and two non-null stimulus conditions comprising an increment stimulus condition characterised by an increment of a parameter relative to the null stimulus condition, and a decrement stimulus condition characterised by a decrement of a parameter relative to the null stimulus condition, wherein said non-null stimulus conditions are presented at a lower frequency relative to said null stimulus condition.

10. The method of claim 9, wherein the parameter is relative stimulus contrast.

11. The method of claim 7, wherein a stimulus sequence comprises a null stimulus condition and a single non-null stimulus condition, wherein said non-null stimulus condition is presented at a lower frequency relative to said null stimulus condition.

12. The method of claim 11, wherein the parameter is luminance.

13. The method of claim 7, wherein the step of presenting (step (a)) comprises:
dividing the visual field of view of each eye of the subject into a plurality of stimulus regions so as to roughly isolate confluent streams within the optic nerve, optic radiations and visual cortex due to their retinotopic arrangement and/or to stimulate different parts of areas of the brain concerned with vision; and
presenting to the two eyes stimuli having different temporal modulation of the appearance of each of the visual field of each eye, the stimuli being different for each of the corresponding regions within the visual field of view of each eye.

14. The method of claim 13, wherein the visual field is divided into quadrants partitioning the visual field along axes defining at least one member selected from the group consisting of the temporal, nasal, inferior and superior visual fields and concentrically organised partitions of these quadrants, which permits separate stimulation of central and peripheral parts of the visual field.

15. The method of claim 13, wherein the stimuli comprise modulation of the luminance or contrast of elements within each of the stimulus regions between two or three luminance levels or between two or three contrast levels.

16. The method of claim 15, wherein the function governing alternation between the levels is approximately uniformly distributed noise.

17. The method of claim 15, wherein the stimuli comprise modulation of an additional parameter selected from the group or position, or apparent depth of colour of elements of the stimulus zones between two or three levels and the function governing alternation between the levels is approximately uniformly distributed noise.

18. The method of claim 1, wherein the temporally modulated stimuli are sufficiently complex so as to permit estimation of linear and non-linear weighting functions characterising the measured responses to each stimulus presented to each part of the nervous system.

19. The method of claim 1, wherein the stimulus sequences comprise aperiodic or pseudorandom stimulus sequences.

20. The method of claim 1, wherein the linear and non-linear weighting functions are Wiener or Volterra kernels.

21. The method of claim 20, wherein the latency to selected peaks within time course of linear kernels and/or the shape of the kernels or their amplitudes are used as measures of the functional status of component parts of the nervous system.

22. An apparatus for assessing the functional status of component parts of the nervous system, comprising:
stimulation means for presenting to the sensory nervous system of a test subject stimulus sequences having different temporal modulation sequences of the appropriate stimulus modality for each stimulated part of the sensory nervous system, the stimuli having different sequences for each stimulated part;
monitoring means for monitoring responses to said stimulus sequences in said test subject; and
processing means for determining coefficients of linear and non-linear weighting functions for each stimulus sequence from the measured responses to said stimuli, wherein the stimulation means comprises means for presenting at least one non-null stimulus condition at an average frequency of between about 0.25 Hz and about 6 Hz.

23. The apparatus of claim 22, wherein the stimulation means comprises means for fluctuating the temporally modulated stimuli between a null stimulus condition and at least one non-null stimulus condition selected from the group consisting of an increment stimulus condition and a decrement stimulus condition, relative to the null stimulus condition, wherein the probability of encountering the null stimulus condition in the stimulus sequences is higher compared to the probability of encountering the at least one non-null stimulus condition, and wherein the temporally modulated stimuli permit estimation of linear and non-linear weighting functions characterising measured responses to each stimulus presented to each part of the nervous system.

24. The apparatus of claim 22, wherein the stimulation means comprises means for presenting a stimulus sequence comprising a null stimulus condition and two non-null stimulus conditions comprising an increment stimulus condition characterised by an increment of a parameter relative to the baseline stimulus condition, and a decrement stimulus condition characterised by a decrement of a parameter relative to the null stimulus condition, wherein said non-null stimulus conditions are presented at a lower frequency relative to said null stimulus condition.

25. The apparatus of claim 22, wherein the stimulation means comprises means for presenting a stimulus sequence comprises a null stimulus condition and a single non-null stimulus condition, wherein said non-null stimulus condition is presented at a lower frequency relative to said null stimulus condition.

26. The apparatus of claim 22, wherein the stimulation means comprises means for presenting the at least one non-null condition at an average frequency of between about 1 and about 6 per second.

27. The apparatus of claim 22, wherein the stimulation means comprises means for stimulating a sensory modality.

28. The apparatus of claim 22, wherein the stimulation means comprises means for stimulating the visual senses.

29. The apparatus of claim 22, wherein the stimulation means comprises means for presenting different luminance levels.

30. The apparatus of claim 22, wherein the stimulation means comprises means for presenting different contrast levels.

31. The apparatus of claim 22, wherein the stimulation means comprises means for presenting different luminance levels.

32. The apparatus of claim 22, wherein the stimulation means comprises means for presenting a stream of separate, viewing images presented to each eye.

33. The apparatus of claim 32, wherein the stimulation means comprises means for presenting to each eye a plurality of stimulus regions so as to roughly isolate confluent streams within the optic nerve, optic radiations and visual cortex due to their retinotopic arrangement and/or to stimulate different parts of areas of the brain concerned with vision.

34. The apparatus of claim 32, wherein the stimulation means further comprises means for presenting to the two eyes stimuli having different temporal modulation of the appearance of each of the visual field of each eye, the stimuli being different for each of the corresponding regions within the visual field of view of each eye.

35. The apparatus of claim 34, wherein the visual field is divided into quadrants partitioning the visual field along axes defining at least one member selected from the group consisting of the temporal, nasal, inferior and superior visual fields and concentrically organised partitions of these quadrants, which permits separate stimulation of central and peripheral parts of the visual field.

36. The apparatus of claim 22, wherein the separate viewing images comprise images of different contrast levels.

37. The apparatus of claim 22, wherein the separate viewing images comprise images of different luminance levels.

38. The apparatus of claim 22, wherein the monitoring means comprises recordal means for recording responses to said stimulus sequences in said test subject.

39. The apparatus of claim 38, wherein the recordal means records visual evoked potentials to provide an objective indication of the said responses.

40. The apparatus of claim 22, wherein the processing means comprises timing means and means for receiving signals from the recordal means indicative of said response.

41. A method of assessing a sensory system of a subject, including:
  simultaneously presenting one or more parts of the sensory system with respective statistically independent sequences of stimuli,
  varying each sequence over time between a null stimulus and one or more less frequent non-null stimuli,
  presenting the non-null stimuli at an average frequency of between about 0.25 Hz and about 6 Hz,
  measuring one or more simultaneous responses by the subject to the sequences of stimuli, and
  determining weight functions from the responses for assessment of the sensory system.

42. A method according to claim 41 wherein the sensory system is a visual, aural or tactile system.

43. An apparatus for assessing a sensory nervous system of a subject, including:
  a stimulator that simultaneously present two or more parts of the sensory system with respective statistically independent sequences of stimuli,
  a monitor that measures one or more simultaneous responses by the subject to the sequences of stimuli, and
  a processor that varies each sequence over time between a null stimulus and one or more less probable non-null stimuli,
  wherein said processor generates the non-null stimuli at an average frequency of between about 0.25 Hz and about 6 Hz, and determines weight functions from the responses for assessment of the sensory system.

44. The apparatus according to claim 43, wherein the sensory system is a visual, aural or tactile system and the stimulator presents optical, audible or tactile patterns to the eyes, ears or skin of the subject.

* * * * *